United States Patent [19]

Clarke et al.

[11] Patent Number: 5,296,245

[45] Date of Patent: * Mar. 22, 1994

[54] PLANT GUM MATERIAL AND USE THEREOF IN FOOD PRODUCTS

[75] Inventors: Adrienne E. Clarke, Parkville; Anthony Bacic, Eltham; Alan G. Lane, Ashfield, all of Australia

[73] Assignee: Bio Polymers Pty. Ltd., Melbourne, Australia

[*] Notice: The portion of the term of this patent subsequent to Jul. 28, 2009 has been disclaimed.

[21] Appl. No.: 920,788

[22] Filed: Jul. 28, 1992

Related U.S. Application Data

[63] Continuation-in-part of Ser. No. 415,263, Oct. 25, 1989, Pat. No. 5,133,979.

[30] Foreign Application Priority Data

Feb. 26, 1987 [AU] Australia .................. PI0556
Sep. 22, 1987 [AU] Australia .................. PI4502

[51] Int. Cl.$^5$ ............................. A23L 1/0532
[52] U.S. Cl. ..................... 426/49; 426/573; 426/577; 435/240.4; 435/240.46; 536/2; 536/3; 536/52; 536/114
[58] Field of Search ........... 426/49, 573, 577, 655, 426/605, 601; 435/240.4, 240.46; 536/2, 3, 52, 114

[56] References Cited

U.S. PATENT DOCUMENTS

5,133,979 7/1992 Clarke .............................. 426/49

FOREIGN PATENT DOCUMENTS

| 0050562 | 3/1984 | European Pat. Off. . |
| 0225496 | 11/1986 | European Pat. Off. . |
| 0285829 | 12/1988 | European Pat. Off. . |
| 0154575 | 4/1982 | Fed. Rep. of Germany . |
| 56164148 | 4/1983 | Japan . |
| 56164149 | 4/1983 | Japan . |
| 60-172927 | 9/1985 | Japan . |
| 60-49604 | 9/1986 | Japan . |
| 61-209599 | 9/1986 | Japan . |

OTHER PUBLICATIONS

Sandford, P. A. and Baird, J. (1983) in "The Polysaccharides" vol. 2, pp. 411–491
McNeil, et al. (1984) Ann. Rev. Biochem. 53:625–663.
Clarke et al. (1979) Phytochemistry 18:521–540.
Fincher et al. (1983) Ann. Rev. Plant Physiol. 34:47–70.
Dubois et al. (1956) Anal. Chem. 28:350–356.
van Holst et al. (1985) Anal. Biochem. 148:446–450.
Bacic et al. (1987) Aust. J. Plant Physiol. 14:633–641.
Meer et al. (1975) Food Tech. 29:22–30.
Barnoud et al. (1977) Physiol. Veg. 15:153–161.
Wallner et al. (1986) J. Amer. Soc. Hort. Sci. 111(5):769–773.
Conrad et al. (1982) Protoplasma 112:196–204.
Olson et al. (1969) Plant Physiol. 44:1594–1600.
Takeuchi et al. (1978) Chem. Abstracts 88:101678z.
Takeuchi et al. (1978) Physiol. Plant 42:21–28.
Aspinall and Molloy (1969) Can. J. Biochem. 47:1063–1070.
Chambat et al. (1987) Food Hydrocolloids 1(516):555–556.

Primary Examiner—Carolyn Paden
Attorney, Agent, or Firm—Greenlee & Winner

[57] ABSTRACT

A method for the culturing of gum-secreting plant cells, recovery of the gum from the medium and use of the plant gum in food products is described. In particular, the plant gum product of cultured Pyrus, *Prunus avium* and Rosa cells can be used in food products as comprising complex carbohydrates and glycoproteins, for example, an emulsifying agent, an emulsion stabilizer, a thickening agent or a texture modifier.

24 Claims, 2 Drawing Sheets

FIG. 2

PLANT GUM MATERIAL AND USE THEREOF IN FOOD PRODUCTS

RELATEDNESS OF THE APPLICATION

The subject application is a continuation-in-part of U.S. Ser. No. 07/415,263, now U.S. Pat. No. 5,133,979, the U.S. national phase of PCT/AU88/00052 having an international filing date of Feb. 26, 1988 and a 35 U.S.C. §371(c) date of Oct. 25, 1989; said PCT/AU88/00052 claiming priority from Australian application PI 0556/87, filed Feb. 26, 1987, and Australian application PI 4502/87, filed September 22, 1987.

FIELD OF THE INVENTION

This invention relates to the use of a plant gum material, produced from plant cells in tissue culture, as an additive to formulations in the food industry. In particular, the present invention relates to the use of this plant gum product as a substitute for gums such as gum arabic (a widely-used emulsion stabilizer) and guar gum (a widely-used thickener) in the food industry, and examples are provided herein of the use of this plant gum product as an emulsion stabilizer, emulsifier, thickening agent and texture modifier, however, the invention is not limited to these uses.

BACKGROUND OF THE INVENTION

Complex carbohydrates and polysaccharides have numerous functions in food products such as emulsifiers, emulsion stabilizers, thickening and gelling agents and suspending agents (Sandford, P. A. and Baird, J. (1983) "The Polysaccharides", Vol. 2. Aspinall, G.0. (ed), Academic Press, N.Y.). Most polysaccharides function by altering the properties of aqueous solutions or dispersions primarily via their ability to bind water molecules and ions; they also interact with each other through "junction zone" formation (Rees, D. A. (1972) Biochem. J. 126:257-273).

Several plant families include species that exude gums, and those that produce copious quantities represent a ready supply of gums. In addition to exudate gums, gums are also obtained from seeds, for example, guar gum, and from algae, e.g., agar. Gums produced as plant exudates or as extracts from seed or other plant materials can require manual harvesting and production can vary with climate and weather conditions.

Gums have been produced by bacterial fermentation under controlled conditions, and xanthan gum which is produced in this manner has recently achieved commercial significance. In general, these gums or mucilages are carbohydrate-enriched polymers of high molecular weight composed of acidic and/or neutral monosaccharide building units joined by glycosidic bonds. One disadvantage associated with xanthan gum production is that, because *Xanthamonas campestris* is a plant pathogen (Schaad N. W. (1982) Plant Disease 66(10):882–890), disposal of cells can present a problem.

Gum arabic is the dried exudate from species of the acacia tree (*Acacia senegal*) found in various tropical and semitropical areas of the world. The acacia trees produce large quantities of gum arabic under adverse conditions, i.e., lack of moisture, poor nutrition and high temperatures. The gum is collected as a natural exudate from the surface of wounds generally produced deliberately in cultivated trees. The exudate is dried to form a product which is graded by its color and contamination with dirt or foreign bodies such as wood or bark (Van Nostrand's Scientific Encyclopedia, 7th ed. (1989) D. Considine (ed.) Vol. I, p. 1389). The dried exudate is completely soluble in hot or cold water, yielding a viscous solution of mucilage finding wide use as an emulsion stabilizer and texture modifier in a wide range of foods, beverages and confectionery and also in adhesives, inks, textiles, printing and cosmetics.

Suspension-cultured plant cells secrete a mixture of complex carbohydrates and glycoproteins into the culture medium. The major classes of complex carbohydrate polymers are proteoglycans (e.g., arabinogalactan-proteins (AGPs)), polysaccharides (e.g., neutral and acidic pectins), hetero-and homo-glucans, heteroxylans, and hetero- and homo-mannans (McNeil et al. (1984) Ann Rev. Biochem. 53:625–663).

Plants of many plant families can be taken into callus (solid) culture and then into liquid suspension culture. It is known that AGPs and other complex carbohydrates and proteins are secreted by many such cell lines (Clarke et al. (1979) Phytochemistry 18:521–540; Fincher et al. (1983) Ann. Rev. Plant Physiol. 34:47–70).

SUMMARY OF THE INVENTION

In accordance with the present invention, the cells of any of the complex carbohydrate-secreting plants are cultured in tissue culture in an appropriate growth medium so that a mixture of complex carbohydrates and (glyco) proteins is secreted into the culture medium. It has now been found that a mixture of these polymers produced by cells derived from tissues of plants in a variety of plant families is a useful substitute for plant gums in the food industry, and may be used, for example, as a substitute for gum arabic as an emulsifying, stabilizing and/or thickening agent. In one particular aspect of the present invention, it has been found that tissue cultures derived from the pear, Pyrus, sweet cherry, *Prunus avium*, and the rose, Rosa, secrete high yields of complex carbohydrates.

According to one aspect of the present invention, there is provided a method for the production of a plant gum product, which comprises the steps of:
a) culturing gum-secreting plant cells in tissue culture in the presence of a culture medium; and
b) recovering the gum product secreted by the cells from the culture medium.

It has been observed that employing BLM as a carbon source increases cell growth and gum yield. It has also been observed that an increase in osmotic pressure or in sucrose concentration in the medium can increase gum production by some cultured plant cells.

The present invention also extends to the plant gum product which can be produced by this method.

According to another aspect, the present invention provides a food product, characterized in that it contains a plant gum product secreted by suspension-cultured plant cells. This product may be either a human or animal food product. "Food product" refers to foods or nutritional supplements that are ingested and consumed and exclude such non-consumables as chewing gum. Pharmaceuticals are excluded from the definition of food products.

The present invention also extends to a method of preparing a food product which is characterized by the use of a plant gum product as outlined above.

In one particular embodiment of the present invention, the food product may comprise a stable emulsion characterized in that it includes a plant gum product as described above as an emulsifying or stabilizing agent. Such a stable emulsion may be used, for example, as a base for a mayonnaise. As is well known in the food industry, a variety of mayonnaises for different purposes (sea foods, egg dishes, green salads, potato salads, etc.) can be prepared using various combinations of colorings and flavorings, which are added to the oil-water mixture before or after emulsifying.

In other embodiments of the invention, the plant gum product may be added to the food product as a thickening or gelling agent, a texture modifier, a binding or coating agent, or the like.

DETAILED DESCRIPTION OF THE INVENTION

As broadly outlined above, the plant gum product which is used as in accordance with the present invention is a product which is secreted by suspension-cultured plant cells. It is preferred that the plant cell used in the subject method produce at least about 0.05% (w/v) gum in the final fermenter culture broth so as to reduce production costs. Plant cell lines that produce at least about 0.5%, 2.0%, and 10.0% (w/v) gum in the final culture broth are increasingly preferred. In one embodiment, the cultured plant cell gums employed in such applications are cultured plant cell gums having arabinogalactan proteins (AGPs) of at least about 4.0% (w/w) in the gum. In some cases, increased AGP concentration in the gum has been found to correlate with enhanced emulsification capacity. A variety of vascular plant cells, including those derived from gymnosperms and angiosperms, may be used in the subject method. Cells of plants of the Dicotyledonae class (e.g., the Rosidae and Asteridae subclasses) and Monocotyledonae class (e.g., the Commelinidae subclass) can be used in the subject method. Pyrus. Prunus, Rosa, Nicotiana and Phleum cell lines can produce gums having the preferred concentrations of polysaccharide and/or AGPs. In particular, *Pyrus communis, Prunus avium, Rosa glauca, Nicotiana olumbaginifolia, Nicotiana alata* and *Phleum pratense* cell lines produce gums that can be useful in the subject method. Gums produced by preferred cell lines can also be used in industrial, pharmaceutical and cosmetic applications, as described in the U.S. application for "Industrial, Pharmaceutical and Cosmetic Applications for Cultured Plant Cell Gums," Ser. No. 07/920,688, on even date herewith, and incorporated herein in its entirety by reference.

In some cases, particular functional properties in the cultured plant cell gum have been associated with particular gum components. It has been observed that AGP in the cultured plant cell gum product can enhance emulsification properties. For example, *Pyrus communis* and *Nicotiana plumbaoinifolia* have higher levels (6–11 % (w/w)) AGPs, while *Phleum pratense* produces a gum with nondetectable AGP and poor gelling and emulsification capacity. *Phleum pratense* has comparable viscosity to Pyrus and Nicotiana gums without the gelling and emulsification properties. *Phleum pratense* is thus useful as a viscosity enhancer in food products where emulsification is not desired.

The cells of a gum-secreting plant, which may for example be initiated from a leaf, style, anther, seed, fruit or stem of the plant, are taken into suspension culture and the gums secreted into the culture mixture are recovered to produce a gum product. The recovery may be by any suitable method such as selective filtration and/or alcohol precipitation.

By way of example of the present invention, the gum product may comprise a material secreted by suspension-cultured cells of the pear (Pyrus). Such cells have been found to secrete a mixture of complex carbohydrates at yields of 5.26 mg carbohydrate/ml of culture fluid as determined by the method of Dubois et al. (1956) Anal. Chem. 28:350–356. The mixture contains 82% neutral monosaccharides and 14% acidic ("pectins") monosaccharides. Acidic residues were determined by the method of Blumenkrantz, N. and Asboe-Hansen, G. (1973) Anal. Biochem. 54:484–489. It also contains approximately 4% protein, as determined by the Bradford, M. (1976) Anal. Biochem. 72:248–254 procedure. In this example, the arabinogalactan-protein (AGP) I5 content of the gum product was 8.9% (w/w) of the total carbohydrate as determined by the single-radial diffusion assay of van Holst, G. J. and Clarke, A. E. (1985) Anal. Biochem. 148:446–450. The neutral monosaccharide composition of one example of this mixture, determined as described in Bacic et 20 al. (1986) Plant Physiology 80:771–777, is as follows:

| Monosaccharide | % w/w |
| --- | --- |
| Rhamnose | 2 |
| Fucose | 3 |
| Arabinose | 16 |
| Xylose | 11 |
| Mannose | 4 |
| Galactose | 18 |
| Glucose | 46 |

In other examples, the same major monosaccharides are present, but the proportions of these and the macromolecules, such as polysaccharides and (glyco)proteins may vary. Arabinose, xylose, galactose and glucose are the major neutral monosaccharides whereas rhamnose, fucose and mannose are characteristically minor neutral monosaccharides.

There is no single measurement or parameter which indicates suitability of a gum product for use in foods. Instead, a number of physical measurements are made (e.g., viscosity, shear rate, gel strength, melting temperature) which, when combined with subjective assessments of palatability (e.g., flavor "body", "mouth feel", stickiness) give an indication as to the likely food uses for the gum product. The following general examples of the use of the gum product prepared from suspension-cultured cells of Pyrus as described above, and compared with gum arabic (a widely-used emulsion stabilizer) and guar gum (a widely-used thickener), are included to illustrate some of the food uses of the product, as follows:

1. Thickening Agent

The gum product exhibits appropriate viscosity and shear thinning properties to make it suitable for use as a thickening agent in food products. The measured viscosity of the gum product was comparable with that of guar gum at the same concentration (0.5% w/v).

Reduced viscosity of the gum product with increasing shear was similar to that seen with guar gum. That is to say, the gum product demonstrated thixotropic properties similar to guar.

Figure 1:
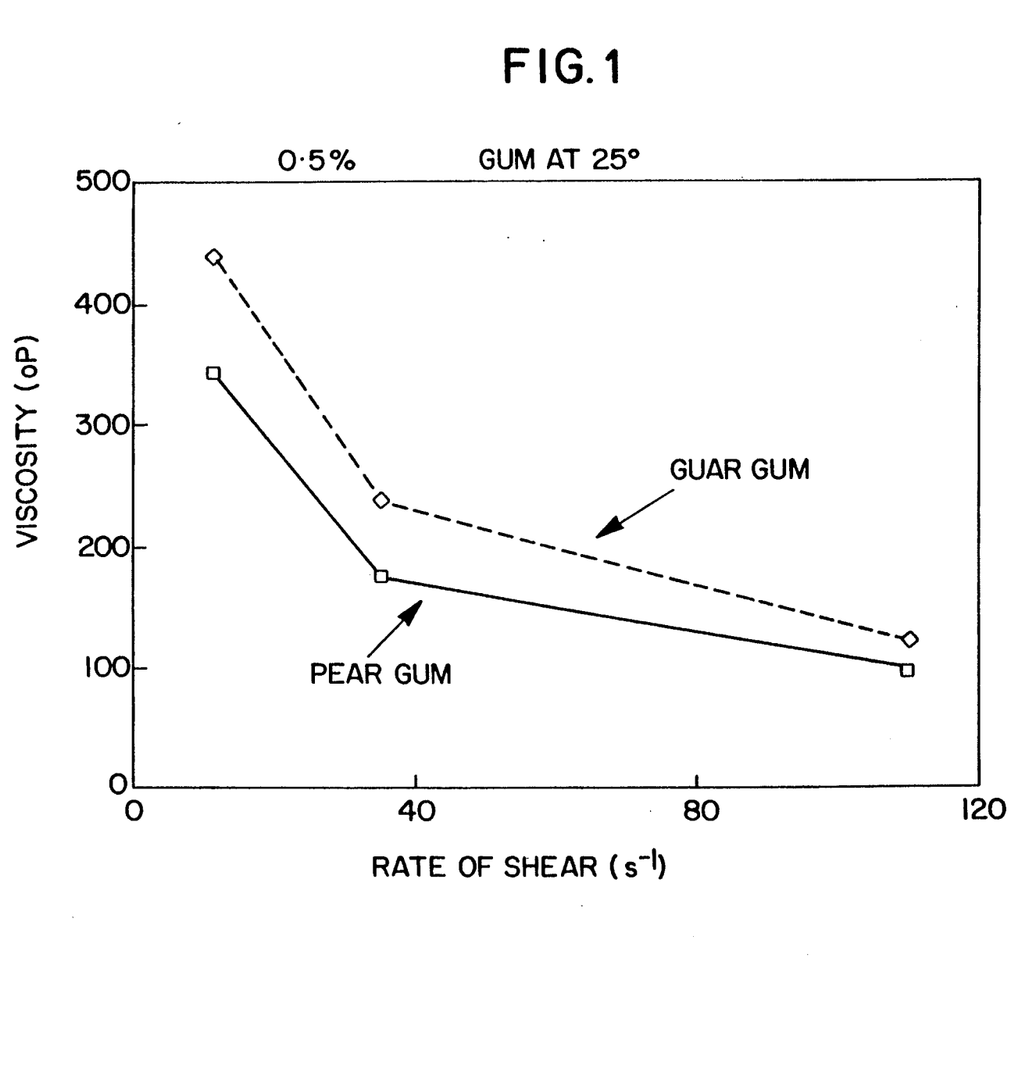
FIG. 1 is a graph of the viscosities of 0.5% (w/v) aqueous mixtures of the subject gum product and of guar gum as a function of sheer rate.

The effect of shear rate on measured viscosity of the gum product and guar gum is shown in FIG. 1.

2. Emulsion Stabilizer/Emulsifier

The gum product at 0.28% (w/v) possessed excellent emulsion stabilizing properties: approximately three times the concentration of gum arabic (1.0% (w/v)) was needed to produce an equivalent emulsion which could be handled without disintegrating and was similar to tofu, bean curd or baked custard in texture and physical strength. However, the gum arabic emulsion obtained at this relatively high concentration (1.0% (w/v)) was not so stable upon storage as that produced by the gum product at the much lower concentration (0.28% (w/v)). In a comparative trial, oil was colored by the addition of an oil-soluble dye, Sudan Black, to allow the effect to be photographed. The results clearly show the oil in the gum arabic emulsion separating and rising to the surface after storage, whereas the emulsion produced by the gum product remains stable, with the oil uniformly distributed throughout.

3. Texture Modifier

The gum product in water (0.5–1.0% w/v) has a good "mouth feel" and almost no flavor, making it wellsuited to incorporation in prepared food formulation. The gel is soft yet coherent and "clean" on the tongue, similar in the mouth to firm yoghurt or a gel of pectin or gelatin. By contrast, a solution of guar at the same concentration had a slimy mouth feel and a strong "beany" flavor.

These general examples of the use of the gum product in food products in accordance with the present invention indicate the potential of gums and emulsion stabilizers produced by plant cell culture for the food industry.

The subject method of food production using cultured plant cell gums can have several advantages over existing food manufacturing methods which use prior art gums. Those advantages include lower production costs, improved purity and improved production reliability. Because the subject food production method uses a cultured plant cell gum product produced in vitro, it does not rely on gum exudates or extracts, which can be more expensive because they are produced by labor-intensive methods. Gum exudates (e.g., gum arabic) must be harvested manually from trees, while seed extracts (e.g., guar gum) are extracted from seeds or other materials harvested from plants. In contrast, cultured plant cell gums used in the subject method can be produced under automated conditions, which can lower associated labor costs and the resulting cost of the cultured plant cell gum.

The subject food production method can also have the advantage of using a gum product that is purer than prior art gums. Because the cultured plant cell gums are produced in fermentation facilities, they can be purer than prior art gums. For example, because gum arabic is hand collected, it is seldom pure; samples are classified according to grade which depends on color and contamination with dirt or with foreign bodies such as wood or bark (VanNostrand's Scientific Encyclopedia (1989), supra).

The subject food production method is also improved in that it relies on a gum product that is produced in fermentation facilities. Since production does not rely on favorable weather conditions, it is more reliable than prior art gum production (see, e.g., Meer et al. (1975) Food Technology 29:22–30). Such reliability of gum results in a more stable and predictable food production cost.

A further advantage of the subject food production method is that it can use smaller quantities of cultured plant cell gum product as compared to prior art gums to achieve comparable effectiveness as emulsifying and stabilizing agents, as film forming or coating agents, or as a protective colloid.

Additionally, the subject food production method has the advantage of using gum-producing cells that do not present the cell disposal problem that can be presented with *X. campestris*.

The suitability of cultured plant cell gums as emulsifying, stabilizing, suspending, thickening, gelling, film-forming, or coating agents or as protective colloids in the subject food production method was unexpected. Because the gums are produced in vitro, it was not known how their compositions or properties would compare to prior art gums, such as gum arabic. The compositions of cultured plant cell gums vary from corresponding plant exudates or extracts (such as those described in Meer et al., supra) in the relative quantities of polysaccharides, glycoproteins and proteoglycans (e.g., AGPs) and in the structures of those components. This unpredictability, i.e., relative ratios and structures of the components of the cultured plant cell gum, clearly argues against the predictability of the composition of the subject plant cell gum and its properties in foods. It was particularly surprising to learn that the subject food production method can use smaller quantities of cultured plant cell gum relative to prior art gums to produce comparable emulsifying, stabilizing, suspending, protecting, etc. effects in the food product.

The following examples illustrate, by way of example only, the production and use of a gum product in accordance with the present invention as an emulsifier, stabilizer, encapsulating agent, thickening agent, etc. in the production of a variety of food products.

All references cited herein are incorporated herein in their entirety by reference.

EXAMPLE 1

A. Production and recovery of gum product.

The gum product secreted from suspension-cultured cells of Pyrus was produced and recovered in the following manner:

Cultivation of cells. Medium (700 ml) in wide-mouth Erlenmyer flasks (2 liters capacity) was sterilized by autoclaving (110° C., 20 minutes) and inoculated with approximately 10% (v/v) of a 7 day-old culture of suspension-cultured cells of Pyrus initiated from callus (solid) culture and growing in the same medium. Flasks were incubated on a rotary shaketable (100 rpm) at 27° C. for 14 days. The composition of the culture medium was as follows, made up to 1 liter with Millipore filtered water:

| | |
|---|---|
| Macro elements stock solution | 10 ml |
| Micro elements stock solution | 1 ml |
| Vitamins stock solution | 1 ml |
| $CaCl_2$ (aqueous - 60 g/l) | 2.5 ml |

| -continued | |
|---|---|
| Fe.EDTA stock solution | 2.5 ml |
| KH$_2$PO$_4$ (aqueous - 17 g/l) | 10 ml |
| Asparagine | 180 mg |
| Ascorbate | 50 mg |
| Thiourea | 25 mg |
| Sucrose | 40 g |
| KI (aqueous - 1.5 g/l) | 0.5 ml |
| 2,4-D (aqueous 2,4-dichlorophenoxy acetic acid - 1 g/l) | 0.5 ml |
| Adjust pH to 5.8–6.0 with KOH. | |

All stock solutions for the media were made up using Milli-Q ™ water deonized water, 18 megaohm, Millipore, Bedford, Mass. in glass bottles. Vitamins and hormone solutions were stored at −20° C.; all other solutions were stored at 1° C.

| Macro elements | |
|---|---|
| NH$_4$NO$_3$ | 165 g |
| KNO$_3$ | 190 g |
| MgSO$_4$.7H$_2$O | 37 g |

The Macro solution was up to 1 liter with water.

| Micro elements | |
|---|---|
| H$_3$BO$_3$ | 1 g |
| ZnSO$_4$.7H$_2$O | 1 g |
| MnSO$_4$.H$_2$O | 1.44 g |
| NaMoO$_4$.2H$_2$O | 0.029 g |
| CuSO$_4$.5H$_2$O | 0.0025 g (*) |
| CoCl$_2$.6H$_2$O | 0.0025 g (*) |

The Micro solution was made up to 100 ml with water. (*) To obtain 2.5 mg of these salts, 25 mg of each was weighed out in separate containers, and dissolved in 10 ml Milli-Q ™ deonized water, 18 megaohm, Millipore, Bedford, Mass.; 1 ml of each solution was then used.

| Vitamins | |
|---|---|
| Ca pantothenate | 0.1 g |
| myo-Inositol | 10.0 g |
| Biotin | 0.001 g (*) |
| Nicotinic acid | 0.001 g (*) |
| Thiamine-HCl | 0.1 g |
| Pyridoxine-HCl | 0.05 g |

The vitamin solution was made up to 100 ml with water. (*) A stock solution containing 1 mg of Biotin + 1 mg of Nicotinic acid per 10 ml was prepared as follows: 10 mg of both vitamins was dissolved in 100 ml of Milli-Q deonized water, 18 megaohm, Millipore, Bedford, Mass.; 10 ml of this solution was used to make up 100 ml of Stock Vitamins.

| Fe.EDTA | |
|---|---|
| FeSO$_4$.7H$_2$O | 6.86 g |
| Na$_2$ EDTA.2H$_2$O | 9.17 g |

The EDTA was dissolved in 1 liter of Milli-Q ™ deonized water, 18 megaohm, Millipore, Bedford, Mass. (magnetic stirrer, room temperature). The ferrous sulphate was dissolved in the EDTA solution. The resulting solution was brought to a boil, cooled and stored in a screw-capped glass bottle at 1° C.

Harvesting and work-up of plant gum product. The culture (2.8 liters) was filtered through a double layer of gauze to remove the cells. The filtrate (fluid) (1.4 liters), containing 5.26 mg of complex carbohydrate/ml was placed in a dialysis sack (approx. 10 cm diameter) and concentrated to approximately half volume using "Carbowax" (polyethylene glycol) at 1° C. for approximately 24 h. The concentrated product was then dialyzed for 24 h against approx. 40 liters of distilled water containing 0.1% (w/v) sodium azide as an antimicrobial agent, followed by 24 h against the same volume of distilled water in which the sodium azide had been omitted. The dialysis was performed under constant mixing conditions by bubbling the water with air from a small air pump. The final volume of the plant gum product was 570 ml. The carbohydrate content of the product was 13 mg/ml.

U.S. patent application Ser. No. 07/920,688 for "Industrial, Pharmaceutical and Cosmetic Applications for Cultured Plant Cell Gums," filed on even date herewith, describes similar gum recovery methods.

B. Preparation of Mayonnaise.

A stable oil-in-water emulsion was prepared, with the gum product secreted from plant cell suspension cultures of Pyrus as emulsifying agent, and used as the base for making a variety of mayonnaise.

Vegetable oil (e.g., Meadowlea ™ blended vegetable oil; 20 ml) was emulsified with 80 ml of aqueous phase containing 0.25–0.5 g of gum product and sufficient acetic acid to provide the desired flavor. Typically, this is obtained by adding 1–3 ml of glacial acetic acid or 10–30 ml of cider vinegar or tarragon vinegar.

The two liquids were emulsified with an emulsifying machine such as an "Ultra-Turrax" (Janke & Kunkel KG), typically on a power setting of 90 volts for 30 seconds, followed by 30 seconds at a setting of 140 volts.

As described above, various combinations of colorings and flavorings may be added to the oil-water mixture before or after emulsifying in order to produce a variety of mayonnaise for different purposes. Examples of colorings and flavorings which have been used in various combinations include tarragon, salt, garlic powder, onion powder, basil, mustard, tahini, MSG, black pepper, paprika and beta-carotene.

EXAMPLE 2

The production of gum product secreted from suspension-cultured cells of Pyrus as described in Example i(a), has been scaled up to a 20 liter glass bottle containing 15 liters of the culture medium as previously described. The medium was inoculated with 2 liters of log phase pear cell suspension-culture and aerated with a sparging device which creates a dispersion of fine bubbles at the bottom of the bottle (air flow 10 l air/min). Following incubation at 27° C. for 14 days, the gum product was harvested and worked-up as described in Example 1(a) to produce a product with similar characteristics to the product of Example 1.

EXAMPLE 3

The Pyrus gum was tested as an encapsulating agent for the flavor oil in a powdered orange drink mix. Pyrus gum was compared to a starch-based encapsulating agent commonly employed in spray-dried flavor oil preparations.

Dry powdered drink mixes were prepared by spray-drying flavor oil emulsions. Flavor emulsions were produced according to the formulations given below:

| Ingredient | Control Mix | Pyrus gum mix |
|---|---|---|
| Maltodextrin (Fielder's PHS 17) | 63.7 g | 91.0 g |
| Encapsulating Agent (N-Lok or Pyrus gum) | 27.3 g | 0.7 g |
| Orange Oil | 20.0 g | 20.0 g |
| EDTA | — | 0.35 g |
| Water | 350 ml | 350 ml |

The chelating agent EDTA was included in the Pyrus gum mix to assist in dissolution of the gum from a freeze dried powder. We have found, with some batches of Pyrus gum, that a small proportion of the gum remains poorly soluble after freeze drying. This is suspected to be due to formation of calcium complexes during freeze drying.

The N-Lok encapsulating agent refers to a starch product produced by the National Starch Company, Australia. N-Lok is currently used as an encapsulating agent for spray-dried flavor oils used in such products as jelly crystals, dessert mixes, cake mixes, drink mixes, packet soup mixes, snack foods, savory dips and spreads. As indicated above, when used to encapsulate citrus oil, a significantly lower concentration of the Pyrus gum mixture encapsulating agent was required relative to the concentration of N-Lok required in the control formulation.

The control mixture was prepared by dissolving the encapsulating agent N-Lok and maltodextrin in water prior to the addition of orange oil. To avoid a possible interaction between the Pyrus gum and the maltodextrin, the Pyrus gum mixture was prepared by adding the orange oil to the hydrated Pyrus gum before the addition of the maltodextrin solution. The Pyrus gum was dissolved in about 200 ml of the water by stirring on a magnetic stirrer and warming to 50°-60° C. The balance of the water was used to dissolve the maltodextrin and the EDTA, using a magnetic stirrer at room temperature. The maltodextrin/EDTA solution was then added to the gum solution and the orange oil added while stirring using a Silverson High Speed Mixer. The mixes were spray-dried in a "baby" Niro Spray Drier, using an inlet temperature of approximately 200° C. and an outlet temperature of 100° C. The spray-drying and control mixing methods are the standard procedures used by Bush Boake Allen in manufacturing spray-dried encapsulated flavor oils.

Despite the use of different mixing regimes and encapsulating agents, no significant differences were noted in the performance of the two encapsulating agents during spray-drying. The pale yellow spray-dried powders were similar in appearance and bulk density. Both were light, free-flowing powders. The Pyrus gum-containing powder was slightly darker in color.

The control and Pyrus gum spray-dried powders were both used in each of two powdered orange drink formulations:

| Ingredient | Percent (w/w) |
|---|---|
| A. Commercial orange drink powder formulation | |
| Caster sugar | 94.5 |
| Citric acid | 3.0 |
| Xanthan gum | 0.4 |
| Sunset Yellow | 0.05 |
| Spray-dried orange flavor powder (containing either Pyrus gum 0.0126 g or N-Lok 0.49 g per 2 g of powder) | 2.0 |
| B. Commercial drink formulation commonly used for taste testing | |
| Sugar | 8 |
| Citric acid | 0.008 |
| Spray-dried orange flavor powder (containing either Pyrus gum 0.0063 g or N-Lok 0.0245 g per 0.1 g of powder) | 0.1 |
| Water | 91.82 |

The four drink mixes (A and B formulations containing control or Pyrus gum spray-dried powders) were evaluated by a panel of 30 tasters who were asked to scale the intensity of orange flavor in unidentified samples presented in random order. Statistical analysis of the data showed that there was no significant difference between perceived intensity of the orange flavor among all four drink mixes, indicating that the Pyrus gum, at significantly lower concentration, has encapsulation properties comparable to N-Lok.

To assess the stability of the spray-dried powders, the oil content of the control and Pyrus gum powders was determined after 3 months and again at 4 months storage at room temperature and a further period of 48 hours at 65° C.

| | Oil Content Percent (w/w) | | |
|---|---|---|---|
| | 3 months | 4 months + 48 h at 65° | Total oil lost |
| N-Lok | 9.92 | 8.67 | 12.6 |
| Pyrus gum | 11.41 | 10.43 | 8.59 |

These results indicate that, over the period of the tests, the powdered oil produced using Pyrus gum was comparable with the N-Lok powdered oil, in terms of both oil content and the stability of the encapsulated oil. The quantity of the two encapsulating agents used to encapsulate the 20 g of oil at 0 months (N-Lok, 27.3 g; Pyrus gum, 0.7 g) indicate that, on a weight for weight basis, Pyrus gum is a much more effective encapsulating agent than N-Lok.

EXAMPLE 4

The Pyrus gum has also been tested as a thickening agent in a strawberry topping. The formulation of the strawberry topping was as follows:

| Ingredient | Percent (w/w) |
|---|---|
| Water | 83 |
| Sugar | 15 |
| Color | 1.4 |
| Flavor | 0.1 |
| Thickening agent | 0.5 |

The coloring was Permicol Red (Bush Boake Allen Number 20.6244) and the flavoring was Quest Strawberry Flavor Number 12651. No fruit was used. The Pyrus gum was dissolved in water by heating to 50°-60°

C. while stirring on a magnetic stirrer. Sugar, color and flavor were then added while stirring and the mixture was allowed to cool.

The Pyrus gum thickening agent conferred desirable consistency to the strawberry topping. Visual comparisons were made with a control topping prepared with 0.2% gum arabic (gum acacia) instead of Pyrus gum. The Pyrus gum-containing product was seen to have an attractive and desirable viscosity, whereas the gum arabic product had a consistency similar to water and was quite unattractive as a topping.

EXAMPLE 5

The Pyrus gum was also tested in a dietetic, non-oil salad dressing as a thickening agent. The formulation of the salad dressing was as follows:

| Ingredient | Percent (w/w) |
|---|---|
| Water | 70 |
| Vinegar | 20 |
| Sugar | 2 |
| Salt | 1 |
| Black pepper | 1 |
| Garlic | 0.5 |
| Mustard | 0.5 |
| Parsley flakes | 2 |
| Bell pepper | 2 |
| Thickening agent | 1 |

Freeze dried thickening agent Pyrus gum was rehydrated by soaking in water from 1 to 18 hours, at room temperature or in the refrigerator, then blended using a domestic food blender. Gentle mixing continued while vinegar, salt, sugar and the herbs and spices were added.

The thickening agent provides the mouthfeel normally provided by the oil content of the dressing. The mouthfeel and flavor were evaluated by one taster and judged to be comparable with that commercially available oil-free salad dressings.

EXAMPLE 6

The Pyrus gum was tested as a stabilizing agent in a chocolate milk mixture to alleviate sedimentation of cocoa powders. The formulation of the chocolate milk was as follows:

| Ingredient | Percent (w/w) |
|---|---|
| Milk | 93 |
| Sugar | 5 |
| Cocoa | 1.8 |
| Stabilizing agent | 0.2 |

The cocoa, sugar and Pyrus gum powders were mixed dry, then added to cold milk while stirring in a domestic food blender.

The Pyrus gum functioned as a stabilizing agent by increasing the viscosity of the milk and slowing sedimentation of particles. A taste panel tried the test chocolate milk and they found that the drink had a viscosity, mouthfeel and taste comparable to the commercial chocolate milk drinks. The commercial chocolate milk drinks use carrageenan as a stabilizing agents.

The product was also compared visually with a commercial chocolate flavored milk, "Big M," made by the Victorian Dairy Industry Authority, which contains carrageenan as the thickening and suspending agent. The two products containing Pyrus gum and carrageenan were very similar visually; both appeared to be equally effective at suspending the cocoa particles.

EXAMPLE 7

The Pyrus gum was employed as a thickening agent in chocolate and vanilla flavored milk desserts having the following formulation:

| Ingredient | Percent (w/w) |
|---|---|
| Chocolate or vanilla flavored milk (Victorian Dairy Industry Authority) | 80 |
| Water | 20 |
| Sodium hexametaphosphate | 0.2 |
| Trisodium citrate | 0.18 |
| Pyrus gum | 0.2 |

The sodium hexametaphosphate is added to stabilize the milk proteins against curdling. The trisodium citrate is added as a sequestering agent to regulate the gelling rate of the Pyrus gum. Sodium hexametaphosphate and trisodium citrate are added to hot milk (about 80° C.) while stirring with a magnetic stirrer. Pyrus gum solution in water (1% w/v) is then added to a final concentration of 0.2% while stirring and the product is allowed to cool. The resulting firm curds were evaluated by one taster, who judged their flavors to be acceptable and their consistencies to be similar to junket.

In addition to the foregoing, the gums of the subject invention can be used for the indicated functions in the following products:

(a) In frozen products such as, for example, ice cream, frozen desserts, soft ices, frozen meat pies, fruit pies, frozen dough and other frozen convenience foods, to confer emulsion stability, viscosity, ice crystal suppression and syneresis suppression.

(b) In baked goods such as, for example, short bread, sweet biscuits, microwaveable cake mixes, cakes, "cracker bread" style biscuits, to maintain texture and moisture and to enhance baking characteristics; as a glaze for cakes, buns, etc.; and to thicken fillings such as artificial cream and fruit jams.

(c) In manufactured or restructured meats or poultry such as, for example, paté, devon/salami style sausages, hot dogs, scotch eggs, turkey "ham", meat loaf, fish fingers, seafood sticks, pet foods and camping foods, as a binder and/or to maintain moisture. It has been found that an aqueous solution containing 0.5% (w/w) of Pyrus gum and 0.036 M calcium citrate forms a firm gel having a shear modulus of approximately 100–200 N/m$^2$, which may e useful in canned or processed meats and pet foods.

(d) In beverages and desserts such as, for example, espresso coffee, milkshakes, mousse, and pressurized whipped cream and cream substitutes as a foaming agent.

(e) In spreads such as, for example, meat spreads, cheese spreads, blended butter, soft margarine and dairy spreads, and lemon curd as an oil-in-water emulsifier and as a water-binder.

(f) In diabetic jam as a gelling agent and to confer viscosity.

(g) In a variety of sauces, dressing and toppings including those described herein and others such as custard, and in prepared milk drinks, to confer viscosity or mouthfeel and as a suspending agent.

(h) In soft drinks such as, for example, sugar-free soft drinks, to confer viscosity or mouthfeel and/or as an emulsion stabilizer.

(i) In dried food formulations such as, for example, dry packet soups, dry pudding mixes, dry dip mixes, dry biscuit mixes, to encapsulate essential oils (e.g., peppermint, herbs and spices) or savory flavors (e.g., "smoky" or "cheese" flavors) and provide stability against evaporation and/or oxidation, slow release of flavor or aroma during cooking, and ease of handling during manufacturing and packaging.

EXAMPLE 9

A comparison of the emulsifying properties of Pyrus gum and a prior art gum, gum arabic, was conducted to determine whether the claimed gum has emulsifying qualities comparable or improved relative to the prior art gum. Aqueous solutions of Pyrus gum and gum arabic were mixed with D-limonene oil to produce emulsions, which were then tested for droplet size, turbidity and shelf life stability.

In order to clarify or reduce complexing of the pectic fraction of the Pyrus gum prior to use, 5 grams of Pyrus gum were dissolved in 500 ml of distilled water and boiled for 5 minutes. Concentrated EDTA solution was added until the insoluble pectic material was dissolved. The solution was filtered through two layers of Whatman glass fiber filter paper GF/F under vacuum and dialyzed (MW cutoff 14,000–16,000) against distilled water at 4° C. for 24 hours. The volume of the solution was then reduced under vacuum by rotary evaporation and freeze dried. Gum arabic was obtained from Sigma, No. G-9752. D-Limonene (p-mentha-1,8-diene) was obtained from Bush Boake and Allen.

Stock solutions of gum arabic (250 mg/ml) and Pyrus gum (62.5 mg/ml or 12.5 mg/ml) were pipetted in duplicate to give final concentrations of 0, 0.2, 0.5, 1, 5, 10 and 20% (w/v). The Pyrus solution could not be prepared at concentrations greater than 5% (w/v) due to its viscosity and gelling properties. Twenty percent D-limonene oil in water emulsions were prepared by injecting the oil into the aqueous solutions under the surface of the solutions while being mixed in an Ultraturrax (Ystal T1500, 25–240V, West Germany) at setting 4 for 15 seconds. The speed of the Ultraturrax was increased to setting 7 for 45 seconds to produce the cloud emulsion. The emulsions were allowed to stand for 0.5 hours to allow bubble dispersal.

To determine emulsion capacity, droplet size, turbidity and shelf-life were measured for each emulsion. Emulsion capacity increases with decreased droplet size, increased turbidity and increased shelf-life stability. The droplet size of the cloud emulsion was examined microscopically by placing 2 drops of the emulsion on a slide and diluting with 2 drops of water and estimating droplet size using a calibrated eye piece graticule. Cloud turbidity was measured by diluting duplicate 5 μl aliquots of cloud emulsion into 5 ml of 0.1% (w/v) sodium dodecylsulphate and measuring absorbance at 500 nm. Cloud emulsions were tested for shelf-life stability by centrifuging at 2,500 rpm for 10 minutes and observation of the resulting separation of oil and water phases. The results are set forth in Tables 1 and 2:

TABLE 1

Droplet size and turbidity measurement

| Conc (% w/v) | | Droplet size (μm) | Turbidity ABS 500 nm | Abs-Avr |
|---|---|---|---|---|
| Gum arabic | | | | |
| 0 | A | Very large | 0.049, 0.023 | 0.022 |
|   | B | Very large | 0.013, 0.003 | |
| 0.2 | A | Very large | 0.006, 0.009 | 0.023 |
|   | B | 10–20 | 0.058, 0.022 | |
| 0.5 | A | 10–20 | 0.042, 0.040 | 0.038 |
|   | B | 4–20 | 0.034, 0.037 | |
| 1 | A | 6–20 | 0.145, 0.130 | 0.128 |
|   | B | 3–12 | 0.125, 0.112 | |
| 5 | A | 1–8 | 0.429, 0.366 | 0.336 |
|   | B | 1–6 | 0.273, 0.277 | |
| 10 | A | 1–10 | 0.482, 0.508 | 0.438 |
|   | B | 1–6 | 0.380, 0.384 | |
| 20 | A | 0.5–3 | 0.505, 0.522 | 0.464 |
|   | B | 1–4 | 0.404, 0.427 | |
| Pear | | | | |
| 0 | A | Very large | 0.049, 0.023 | 0.022 |
|   | B | Very large | 0.013, 0.003 | |
| 0.2 | A | 1–20 | 0.150, 0.136 | 0.127 |
|   | B | 2–20 | 0.115, 0.110 | |
| 0.5 | A | 1–8 | 0.187, 0.181 | 0.183 |
|   | B | 2–20 | 0.173, 0.194 | |
| 1 | A | 1–8 | 0.240, 0.223 | 0.252 |
|   | B | 1–6 | 0.275, 0.270 | |
| 5 | A | 1–2 some larger | 0.577, 0.592 | 0.653 |
|   | B | 1–3 some larger | 0.776, 0.670 | |

Figure 2:
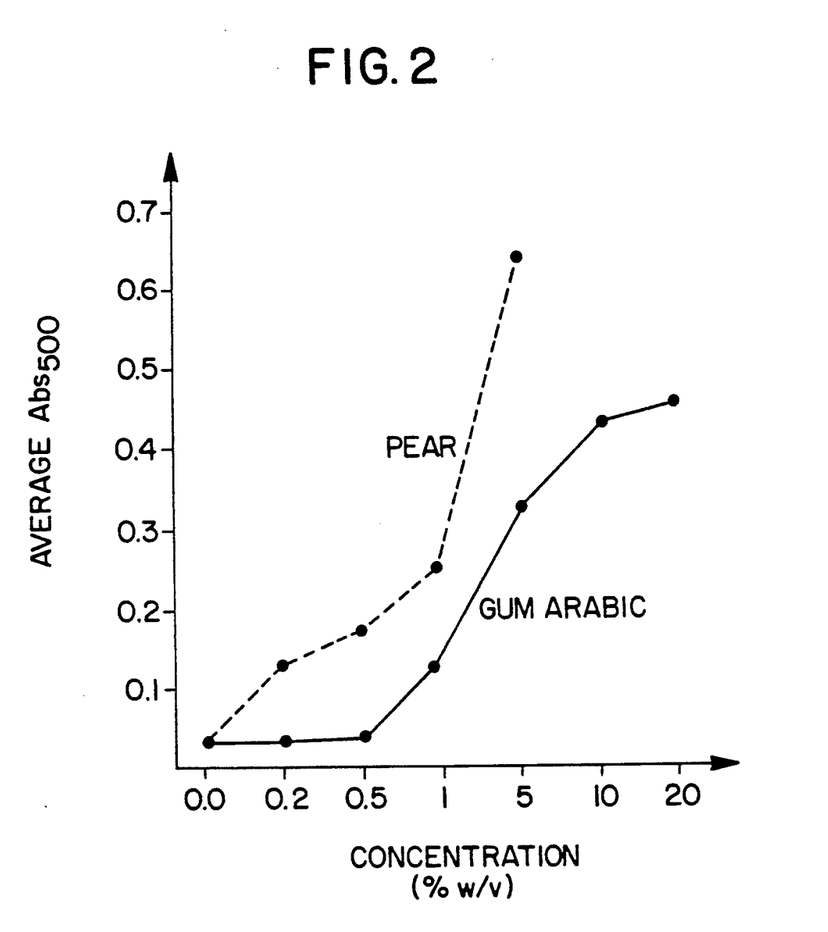
FIG. 2 is a graph comparing the turbidity of oil in water emulsions using cultured Pyrus gum and gum arabic. As discussed in Example 9, turbidity is one indicator of emulsion-forming capacity.

*A and B are duplicates.
The Table I results are graphed in FIG. 2.

TABLE 2

Shelf life stability

| Conc (% w/v) | Emulsion Description[1] | |
|---|---|---|
| | Before | After centrifugation |
| Gum arabic | | |
| 0 | Oil layer | Oil layer |
|   | Water layer | Water layer |
| 0.2 | Oil film | Oil layer |
|   | Cream layer | Water layer |
|   | Water layer | |
| 0.5 | Oil film | Oil layer |
|   | Cream layer | Water layer |
|   | Water layer | |
| 1 | Cream layer | Oil layer |
|   | Water layer | Cream layer |
|   | | Water layer |
| 5 | Cream layer | Cream layer |
|   | Water layer | Water layer |
| 10 | Cream layer | Cream layer |
|   | Water layer | Water layer |
| 20 | Cream layer | Cream layer |
|   | Water layer | Water layer |
| Pear | | |
| 0 | Oil layer | Oil layer |
|   | Water layer | Water layer |
| 0.2 | Oil film | Oil film |
|   | Cream layer | Cream layer |
|   | Water layer | Water layer |
| 0.5 | Oil film | Oil film |
|   | Cream layer | Cream layer |
|   | Water layer | Water layer |
| 1 | Cream layer | Cream layer |
|   | Water layer | Water layer |
| 5 | Cream | Cream |

[1]Descriptions taken from duplicate emulsions.

From the foregoing results, it is seen that when emulsifying 20% D-limonene in water, Pyrus gum on a weight for weight basis produces smaller droplets at a lower concentration than gum arabic. For example, at 0.2% (w/v) of Pyrus gum, the emulsion mixture has a film of free oil, a cream layer stable to centrifugation, oil droplets of 1-20 μm and a cloud turbidity at 500 nm of 0.127. In contrast, 0.2% (w/v) gum arabic in an emulsion mixture has an unstable cream which separates completely to oil on centrifugation, has a larger droplet size (10-20 μm) and an average cloud turbidity reading of 0.023 at 500 nm. These results indicate that the Pyrus gum has improved emulsifying qualities relative to those of gum arabic at the same concentration.

Those skilled in the art will appreciate that the invention described herein is susceptible to variations and modifications other than those specifically described. It is to be understood that the invention includes all such variations and modifications which fall within its spirit and scope.

We claim:

1. A method of making a food product which comprises the step of adding a cultured plant gum of a vascular plant cell to a food or nutritional supplement.

2. A method of making a food product which comprises a step of adding an agent selected from the group consisting of an emulsifying agent, an emulsion stabilizer, a thickening agent, a gelling agent, a texture modifier, an encapsulation agent, and a combination thereof, to a food or nutritional supplement wherein said agent comprises a cultured plant gum of a vascular plant cell.

3. The method of claim 2 wherein said gum functions as a thickening agent.

4. The method of claim 2 wherein said gum functions as gelling agent.

5. The method of claim 2 wherein said gum functions as a texture modifier.

6. The method of claim 2 wherein said gum functions as an emulsifying agent.

7. The method of claim 2 wherein said gum functions as an emulsion stabilizer.

8. The method of claim 2 wherein said gum functions as an encapsulating agent.

9. The method of claim 2 wherein said gum is produced by culturing Pyrus cells in a culture medium.

10. The method of claim 9 wherein said cells comprise *P. communis* cells.

11. The method of claim 2 wherein said gum is produced by culturing Prunus cells in a culture medium.

12. The method of claim 11 wherein said cells comprise *P. avium* cells.

13. The method of claim 2 wherein said gum is produced by culturing Rosa cells in a culture medium.

14. The method of claim 13 wherein said cells comprise *R. glauca* cells.

15. The method of claim 2 wherein said gum is produced by culturing Nicotiana cells in a culture medium.

16. The method of claim 15 wherein said cells comprise *N. alata* or *N. plumbaginifolia*.

17. The method of claim 2 wherein said gum is produced by culturing Phleum cells in a culture medium.

18. The method of claim 17 wherein said cells comprise *P. pratense* cells.

19. The method of claim 2 wherein said cultured plant cell gum is produced by the steps of:
   (a) culturing a vascular plant cell to produce a culture broth; and
   (b) recovering from said broth said cultured plant cell gum.

20. The method of claim 19 wherein said culture broth comprises a gum concentration of at least about 0.05% (w/v) cultured plant cell gum.

21. The method of claim 19 wherein said gum comprises at least about 4.0% (w/w) arabinogalactan proteins.

22. The method of claim 2 wherein said food product is selected from the group consisting of mayonnaise, powdered drink mix, fruit-flavored topping, salad dressing, chocolate milk drink, flavored milk desserts, frozen foods, bakes goods, manufactured or restructured meats, espresso coffee, whipped cream, meat spreads, cheese spreads, blended butter, soft margarine, dairy spreads, lemon curd, diabetic jam, custard, soft drinks and dried food formulations.

23. In a method of making a food product which comprises a step of adding an agent selected from the group consisting of an emulsifying agent, an emulsion stabilizer, a thickening agent, a gelling agent, a texture modifier, an encapsulation agent, and a combination thereof, to a food or nutritional supplement the improvement comprising employing a cultured plant cell gum of a vascular plant cell as said agent.

24. The method of claim 23 wherein the improvement comprises adding a lesser amount of a cultured plant cell gum of a vascular plant cell as said emulsifying agent, emulsion stabilizer, thickening agent, gelling agent, texture modifier, or encapsulation agent.

* * * * *

UNITED STATES PATENT AND TRADEMARK OFFICE
CERTIFICATE OF CORRECTION

PATENT NO. : 5,296,245
DATED : Mar. 22, 1994
INVENTOR(S) : Clarke et al.

It is certified that error appears in the above-indentified patent and that said Letters Patent is hereby corrected as shown below:

```
At column 7, line 8, in the second column of the Table listing
the amount of 2,4-D, replace [0.5 ml] with --1 ml--.
```

Signed and Sealed this

Sixth Day of September, 1994

Attest:

BRUCE LEHMAN

*Attesting Officer*    *Commissioner of Patents and Trademarks*